(12) United States Patent
Bjelke

(10) Patent No.: US 9,896,677 B2
(45) Date of Patent: Feb. 20, 2018

(54) PURIFICATION OF BLOOD COAGULATION FACTORS

(75) Inventor: Jais Rose Bjelke, Smoerum (DK)

(73) Assignee: NOVO NORDISK HEALTH CARE AG, Zurich (CH)

(*) Notice: Subject to any disclaimer, the term of this patent is extended or adjusted under 35 U.S.C. 154(b) by 362 days.

(21) Appl. No.: 13/522,548

(22) PCT Filed: Jan. 18, 2011

(86) PCT No.: PCT/EP2011/050594
§ 371 (c)(1),
(2), (4) Date: Sep. 10, 2012

(87) PCT Pub. No.: WO2011/086197
PCT Pub. Date: Jul. 21, 2011

(65) Prior Publication Data
US 2013/0034896 A1 Feb. 7, 2013

(30) Foreign Application Priority Data
Jan. 18, 2010 (EP) .................... 10150980

(51) Int. Cl.
*C12N 9/48* (2006.01)
*C12N 9/64* (2006.01)
*C07K 14/745* (2006.01)

(52) U.S. Cl.
CPC ............ *C12N 9/647* (2013.01); *C07K 14/745* (2013.01); *C12N 9/644* (2013.01); *C12Y 304/21022* (2013.01)

(58) Field of Classification Search
USPC ....................................................... 362/105
See application file for complete search history.

(56) References Cited

U.S. PATENT DOCUMENTS

| | | | |
|---|---|---|---|
| 4,902,614 A | 2/1990 | Wakabayashi et al. | |
| 5,252,709 A | 10/1993 | Burnouf et al. | |
| 5,633,350 A | 5/1997 | Fischer et al. | |
| 6,258,938 B1 | 7/2001 | Furie et al. | |
| 6,280,729 B1 | 8/2001 | Huang et al. | |
| 7,276,590 B1 | 10/2007 | Staby | |
| 7,439,025 B2 | 10/2008 | Stenflo et al. | |
| 2008/0207879 A1 | 8/2008 | Artur et al. | |
| 2011/0287518 A1 | 11/2011 | Bjelke | |

FOREIGN PATENT DOCUMENTS

| CN | 101098883 A | | 1/2008 |
|---|---|---|---|
| EP | 363126 A2 | | 4/1990 |
| EP | 617049 A1 | | 9/1994 |
| EP | 10150980 | * | 1/2010 |
| RU | 2364626 C2 | | 8/2009 |
| WO | 2007/065173 A2 | | 6/2007 |

OTHER PUBLICATIONS

Wajih et al. J Biol Chem., Sep. 9, 2005;280(36):31603-7. Epub Jul. 19, 2005.*
Paul. Fundamental Immunology, (textbook), 1993, pp. 292-295, under the heading "Fv Structure and Diversity in Three Dimensions".*
Gillis, S et al. "Gamma-Carboxyglutamic acids 36 and 40 do not contribute to human factor IX function" (1997) Protein Sci vol. 6: 185-96.
Liebman, Ha "The factor IX phospholipid-binding site is required for calcium-dependent activation of factor IX by factor Xia" (1987) J Biol Chem vol. 262: 7605-7612.
Liebman, Ha "The metal-dependent conformational changes in Factor IX associated with phospholipid binding" (1993) Eur J Biochem vol. 212: 339-345.
Hoffman and Monroe, Thrombosis and Haemostasis, "A Cell-Based Model of Hemostasis", 2001, vol. 85, Number -, pp. 958-965.
Little, "Displacement Chromatography Comes of Age", Chromatography Techniques, 2008, pp. 21-23.
Kaufman et al., "Expression, Purification, and Characterization of Recombinant g-Carboxylated Factor IX Synthesized in Chinese Hamster Ovary Cells", Journal of Biological Chemistry, 1986, vol. 261, No. 21, pp. 9622-9628.
Schmidt et al, "Structure-Function Relationships in Factor IX and Factor IXa", Trends in Cardiovascular Medicine, 2003, vol. 13, No. 1, pp. 39-45.
Wajih et al., "Increased Production of Functional Recombinant Human Clotting Factor IX by Baby Hamster Kidney Cells Engineered to Overexpress VKORC1, The Vitamin K 2,3-Epdxide-Reducing Enzyme of the Vitamin K Cycle", Journal of Biological Chemistry, 2005, vol. 280, No. 36, pp. 31603-31607.
Ohsawa et al., "Purification of Sufficiently g-Carboxylated Recombinant Protein C and its Derivatives", Journal of Chromatography, 1992, vol. 597, pp. 285-291.
Nakamura et al., "Immunoaffinity Purification of Protein C by Using Conformation-Specific Monoclonal Antibodies to Protein C-Calcium Ion Complex", Biochimica Et Biophysica Acta, 1987, vol. 925, pp. 85-93.
Van Cott et al., "Affinity Purification of Biologically Active and Inactive Forms of Recombinant Human Protein C Produced in Porcine Mammary Gland", Journal of Molecular Recognition, 1996, vol. 9, pp. 407-414.
Lindsay et al., Journal of Chromatography, 2004, vol. 1026, No. 1-2, pp. 149-157.

(Continued)

Primary Examiner — Christian Fronda
(74) Attorney, Agent, or Firm — Leon Y. Lum

(57) ABSTRACT

The present invention relates to the purification of vitamin K-dependent blood coagulation factors, such as Factor IX (FIX). In particular, the invention provides a method for purifying Factor IX having a desired content of gamma-carboxyglutamic acid from a sample comprising a mixture of species of said Factor IX having different contents of gamma-carboxyglutamic acid, said method comprising the steps of: (a) loading said Factor IX sample onto an immunoaffinity chromatography material coupled to a binding moiety for gamma-carboxyglutamic acid; (b) eluting said Factor IX; and (c) selecting a fraction obtained from said elution wherein the polypeptides in the fraction have the desired content of gamma-carboxyglutamic acids; characterized in that the total concentration of Factor IX within said sample exceeds the binding ability of the immunoaffinity chromatography material.

19 Claims, 6 Drawing Sheets

(56) References Cited

OTHER PUBLICATIONS

Malmquist et al., Journal of Chromatography, 1992, vol. 627, No. 1-2, pp. 107-124.
Malhotra et al., Biochimica Et Biophysica Acta, 1983, vol. 746, No. 1-2, pp. 81-86.
Yan et al., Nature Biotechnology, 1990, vol. 8, No. 7, pp. 655-661.
Burnier et al., Molecular and Cellular Biochemistry, 1981, vol. 39, No. 2, pp. 191-207.
Malhotra et al., Biochemistry and Cell Biology, 1990, vol. 68, No. 4, pp. 705-715.
Osterud et al., Journal of Biological Chemistry, 1978, vol. 253, No. 17, pp. 5946-5951.
Linde et al., "Evidence for Several Gamma Carboxyglumatic Acid-Containing Proteins in Dentin", Biochimica Et Biophysica Acta, 1982, vol. 704, No. 2, pp. 235-239.
Amersham Biosciences Ion Exchange (IEX) Chromatography, Protein Purification Handbook, Year 2001 pp. 71-76.
Wang Jianhua, et al., "Development of Human High Purity Coagulation Factor IX", Chinese Journal of Hematology, 1993, vol. 14, No. 10, pp. 527-529.

* cited by examiner

```
Factor VII   ANA-FL**LRPGSL*R*CKQCSFAR*IFKDA*RTKLFWISY
Factor IX    YNSGKL**FVQGNL*R*CMKCSFAR*VF*NT*RTT*FWKQY
Factor X     ANS-FL**MKKGHL*R*CMTCSYAR*VF*DSDKTN*FWNKY
```

Fig. 1B

SEQUENCE LISTING

```
<160> NUMBER OF SEQ ID NOS: 4

<210> SEQ ID NO 1
<211> LENGTH: 445
<212> TYPE: PRT
<213> ORGANISM: Mouse

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Asn Ser Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ile Gly Lys Pro Thr Tyr Asp Asp Asp Phe
    50                  55                  60

Lys Gly Arg Phe Ala Phe Ser Leu Glu Thr Ser Ala Ser Thr Val Tyr
65                  70                  75                  80

Leu Gln Ile Asn Asn Leu Lys Asn Glu Asp Thr Ala Thr Tyr Phe Cys
                85                  90                  95

Thr Arg Gly Gly Leu Tyr Asp Gly Tyr Pro Ser Phe Asp Tyr Trp Gly
            100                 105                 110

Gln Gly Thr Ala Leu Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
```

```
                    180                 185                 190
Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
        210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 2
<211> LENGTH: 213
<212> TYPE: PRT
<213> ORGANISM: Mouse

<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Ser Tyr Tyr Cys Gln Gln Trp Ser Ser Asn Pro Arg Thr
                85                  90                  95

Phe Gly Gly Gly Thr Lys Leu Glu Ile Lys Arg Ala Asp Ala Ala Pro
            100                 105                 110
```

```
Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Arg Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 3
<211> LENGTH: 415
<212> TYPE: PRT
<213> ORGANISM: Homo sapiens

<400> SEQUENCE: 3

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270
```

```
Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 4
<211> LENGTH: 18
<212> TYPE: PRT
<213> ORGANISM: Homo Sapiens

<400> SEQUENCE: 4

Arg Lys Pro Arg Asn Leu Ile Lys Asn Ala Asn Glu His Asp Leu Phe
1               5                   10                  15

Val Thr
```

PURIFICATION OF BLOOD COAGULATION FACTORS

CROSS-REFERENCE TO RELATED APPLICATIONS

This application is a 35 U.S.C. § 371 national stage application of International Patent Application PCT/EP2011/050594 (published as WO 2011/086197 A1), filed Jan. 18, 2011, which claimed priority of European Patent Application 10150980.0, filed Jan. 18, 2010; this application further claims priority under 35 U.S.C. § 119 of U.S. Provisional Application 61/297,011, filed Jan. 21, 2010.

FIELD OF THE INVENTION

The present invention relates to the purification of gamma carboxylated forms of proteins/polypeptides specifically vitamin K-dependent blood coagulation factors, such as Factor IX (FIX). In particular, the present invention relates to methods utilising immunoaffinity chromatography, by which different gamma carboxylated forms of proteins/polypeptides, specifically vitamin K-dependent blood coagulation factors, such as Factor IX (FIX), can be purified.

INCORPORATION-BY-REFERENCE OF THE SEQUENCE LISTING

In accordance with 37 C.F.R. § 1.52(e)(5), Applicants enclose herewith the Sequence Listing for the above-captioned application entitled "7915204US_Seq_Listing_ST25", created on Jun. 13, 2012 and modified on Jan. 31, 2017. The Sequence Listing is made up of 9,901 bytes, and the information contained in the attached "7915204US_Seq_Listing_ST25" is identical to the information in the specification as originally filed. No new matter is added.

BACKGROUND OF THE INVENTION

Blood coagulation is a process consisting of a complex interaction of various blood components, or factors, which eventually gives rise to a fibrin clot. Generally, the blood components that participate in what has been referred to as the coagulation "cascade" are proenzymes or zymogens, enzymatically inactive proteins that are converted to proteolytic enzymes by the action of an activator, which is itself an activated clotting Factor. Coagulation factors that have undergone such a conversion are generally referred to as "active factors", and are designated by the addition of a lower case "a" suffix (e.g., Factor VIIa).

Activated Factor X ("Xa") is required to convert prothrombin to thrombin, which then converts fibrinogen to fibrin as a final stage in forming a fibrin clot. There are two systems, or pathways, that promote the activation of Factor X. The "intrinsic pathway" refers to those reactions that lead to thrombin formation through utilisation of factors present only in plasma. A series of protease-mediated activations ultimately generates Factor IXa, which, in conjunction with Factor VIIIa, cleaves Factor X into Xa. An identical proteolysis is effected by Factor VIIa and its co-Factor, tissue factor, in the "extrinsic pathway" of blood coagulation. Tissue factor is a membrane bound protein and does not normally circulate in plasma. Upon vessel disruption, however, it can complex with Factor VIIa to catalyse Factor X activation or Factor IX activation in the presence of $Ca^{2+}$ and phospholipid. The relative importance of the two coagulation pathways in haemostasis is still unclear.

Factor IXa (FIXa) is a trypsin-like serine protease that serves a key role in haemostasis by generating, as part of the Xase complex, most of the Factor Xa required to support proper thrombin formation during coagulation (reviewed in Hoffman M. and Monroe D. M., III (2001) A cell-based model of hemostasis. Thromb Haemost 85, 958-965). Congenital deficiency of Factor IXa activity is the cause of the X-linked bleeding disorder haemophilia B affecting approximately 1:100,000 males. These haemophilia patients are currently treated by replacement therapy with either recombinant or plasma-derived coagulation Factor IX.

Factor IX is a vitamin K-dependent coagulation factor with structural similarities to Factor VII, Factor X, and protein C. The circulating zymogen form, which has a plasma half-life of about 18-30 hours, consists of 415 amino acids divided into four distinct domains comprising an N-terminal γ-carboxyglutamic acid rich (Gla) domain, two EGF domains, and a C-terminal trypsin-like serine protease domain. Activation of Factor IX occurs by limited proteolysis at $Arg^{145}$-$Ala^{146}$ and $Arg^{180}$-$Val^{181}$ releasing a 35-aa fragment, the so-called activation peptide (Schmidt A. E. and Bajaj S. P. (2003) Structure-function relationships in Factor IX and Factor IXa. Trends Cardiovasc Med 13, 39-45). The activation peptide is heavily glycosylated containing two N-linked and up to four O-linked glycans.

γ-Carboxyglutamic acid (Gla) is a unique amino acid that binds to calcium. It is a modified form of glutamic acid (Glu) and can be produced in vivo by the post-translational modification of glutamate residues. Carboxylation of glutamic acid in this way enables calcium binding and allows the attachment of proteins such as procoagulants and anticoagulants to phospholipids. This enzyme-mediated reaction, known as γ-carboxylation (gamma carboxylation), requires vitamin K as a cofactor.

Some mature proteins contain a domain that is rich in amino acids that have been converted to γ-carboxyglutamic acid in this way. This is known as a GLA domain. This GLA domain is often responsible for the high-affinity binding of calcium ions by the protein. Such a GLA domain may be found in a variety of different proteins. For example, blood coagulation Factors VII, IX and X and prothrombin all include a GLA domain that comprises a number of Gla amino acid residues.

Van Cott et al (1996) Journal of Molecular Recognition 9, 407-414 describes affinity purification of biologically active and inactive forms of recombinant Human Protein C.

Full gamma-carboxylation of the 12 Glu residues in the Gla domain of FIX in recombinant production represents a major challenge. FIX produced in Chinese hamster ovary (CHO) cells shows a specific activity of FIX of approx. 50%, an activity level which correlates with the degree of gamma-carboxylation of FIX expressed from the cell line. There is therefore a need to develop a downstream separation method to remove FIX species with suboptimal gamma-carboxylated Gla domain.

SUMMARY OF THE INVENTION

The present inventors have found that it is possible to separate or purify different species of Factor IX where the different species vary in the amount of gamma carboxylation, or in the number of gamma carboxyglutamic acid residues that they contain. The invention addresses in particular the chromatographic separation of Factor IX species having different contents of gamma-carboxyglutamic acid.

Thus, the invention provides a method for purifying Factor IX having a desired content of gamma-carboxyglutamic acid from a sample comprising a mixture of species of said Factor IX having different contents of gamma-carboxyglutamic acid, said method comprising the steps of:
(a) loading said Factor IX sample onto an immunoaffinity chromatography material containing a coupled antibody, which has a binding moiety for gamma-carboxyglutamic acid;
(b) eluting said Factor IX; and
(c) selecting a fraction obtained from said elution wherein the Factor IX polypeptides in the fraction have the desired content of gamma-carboxyglutamic acids;
characterised in that the total concentration of Factor IX within said sample exceeds the binding ability of the immunoaffinity chromatography material.

The method may comprise selecting a fraction obtained from said elution which has an increase in the proportion of #1-11-Gla and/or #1-12-Gla forms of Factor IX compared with the proportion of #1-11-Gla and/or #1-12-Gla forms of Factor IX in the sample being purified.

The method may also comprise selecting a fraction obtained from said elution which has a decrease in the proportion of #1-10-Gla form of Factor IX compared with the proportion of #1-10-Gla form of Factor IX in the sample being purified.

The present invention also extends to Factor IX formulations obtained by the methods as described herein, i.e. formulations in which the amount of one or more species of Factor IX have been altered, where the species differ in the extent of gamma carboxylation, or in the number of gamma carboxyglutamic acid residues that they contain.

BRIEF DESCRIPTION OF THE FIGURES

FIG. 1B shows an alignment of part of the amino acid sequences of the human Factor VII, Factor IX and Factor X polypeptides. These alignments are derived from the GLA domain of each of these polypeptides and show the location of Gla residues as *.

DETAILED DESCRIPTION OF THE INVENTION

The present invention derives from the findings that Factor IX species having different levels of gamma carboxylation may have different levels of activity and that such different species can be purified or separated using immunoaffinity chromatography. By increasing the proportion of more active Factor IX species, and/or by decreasing the proportion of less active or inactive Factor IX species in a sample, this can result in the production of a purified formulation having increased specific activity.

Figure 1A:
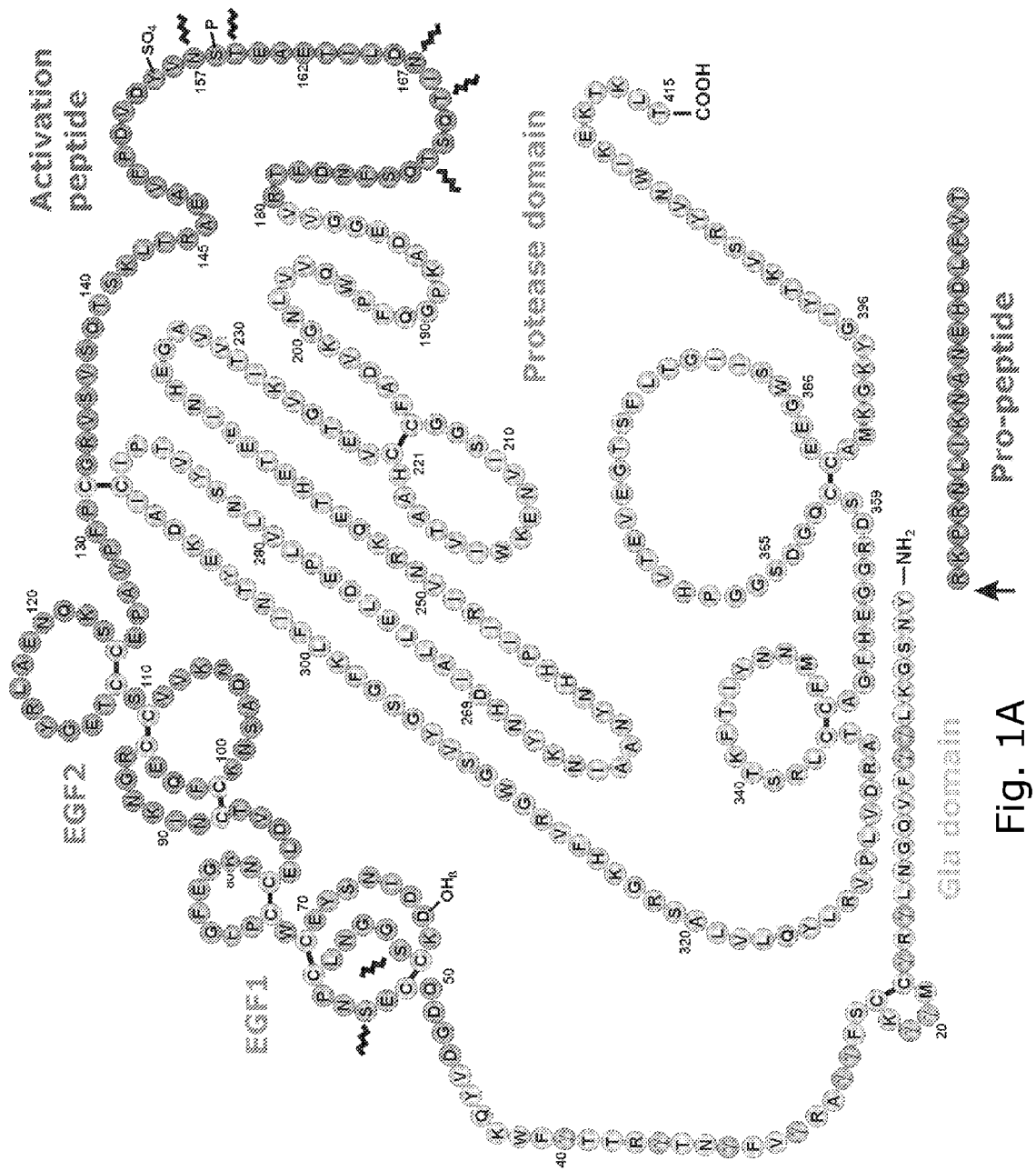
FIG. 1A shows the primary structure of human Factor IX (SEQ ID NO: 3) with sub-domains identified and propeptide (SEQ ID NO:4). The GLA domain is found at amino acids 1-46; the EGF1 domain is found at amino acids 47-83, the EGF2 domain is found at amino acids 84 to 124, the activation peptide is found at amino acids 146 to 180 and the protease domain is found at amino acids 181 to 415. The 12 amino acids in the Gla domain that are potentially subject to gamma-carboxylation are labelled as "γ" and are located at amino acids 7, 8, 15, 17, 20, 21, 26, 27, 30, 33, 36 and 40.

In particular, FIG. 1A shows the primary structure of human Factor IX protein. This protein includes a GLA domain at amino acids 1 to 46. This domain includes 12 amino acid residues that can be modified from glutamate to Gla. These are located at positions 7, 8, 15, 17, 20, 21, 26, 27, 30, 33, 36 and 40. It is therefore capable of comprising up to 12 Gla residues. The polypeptide to be purified in accordance with the present invention is therefore Factor IX. FIG. 1B shows an alignment based on the Gla domain of human Factor VII, IX and X proteins. The locations of the amino acid residues that can be modified from glutamate to Gla in each sequence are identified as *.

It will be appreciated that the purification process of the invention may equally apply to a polypeptide which comprises a GLA domain from a known gamma carboxylated protein. A number of polypeptides comprising GLA domains are known. A number of blood clotting and regulatory proteins, including prothrombin, Factor VII, Factor IX, Factor X, Prothrombin, Protein C and Protein S, include Gla residues. These proteins can contain 10 to 12 gamma carboxyglutamic acid residues in the GLA domain, located within the first 40 residues of the N-terminus of the mature protein. Bone proteins such as osteocalcin and Matrix Gla protein and other mammalian vitamin K dependent proteins such as growth arrest-specific-6 (Gash), Protein Z, proline-rich-Gla-1 (PRGP1), proline-rich-Gla-2 (PRGP2), proline-rich-Gla-3 (PRGP3) and proline-rich-Gla-4 (PRGP4) also comprise multiple Gla residues. Gamma carboxyglutamic acid residues have also been found in non-mammalian proteins, such as the conopeptides Conantokin G and Conantokin T. Any of these polypeptides may be purified in accordance with the invention.

As discussed further below, the methods of the invention allow for the purification of different molecular species of Factor IX in which different levels of gamma carboxylation have occurred. The numbers referred to here are the total number of Gla residues that may be present in Factor IX. That is, if Factor IX is fully gamma carboxylated, these numbers indicate the number of Gla residues that are present. For example, where gamma carboxylation takes place in the GLA domain, these numbers refer to the total number of possible sites for gamma carboxylation in that GLA domain, such as the total number of Glu residues in the translated Factor IX or the maximum number of Gla residues that may be produced by the action of an enzyme such as γ-glutamyl carboxylase. Additional species of the same Factor IX entity may also exist in which fewer gamma carboxyglutamic acid residues than this maximum are present.

Factor IX may therefore comprise multiple Glu residues in the N-terminal 40 residues of its translated amino acid sequence. For example, the amino acid sequence of the expressed Factor IX may comprise 2, 3, 4, 5, 6, 7, 8, 9, 10, 11, 12 or more Glu residues in the 40 amino acids closest to the N terminus of Factor IX, or in the 40 amino acids closest to the N terminus of the mature protein.

Gamma carboxylation may be achieved using an enzyme. Such a γ-glutamyl carboxylase enzyme is known to be involved in the gamma carboxylation of many polypeptides in vivo. γ-Glutamyl carboxylase is an endoplasmic enzyme which catalyses the post-translational modification of Glu into Gla in the GLA domain of a number of vitamin K dependent coagulation factors. The Factor IX polypeptides for use in the present invention may thus be identified by determining whether they are gamma carboxylated by γ-glutamyl carboxylase.

The γ-glutamyl carboxylase enzyme is believed to bind to its substrate protein via a sequence motif on the amino terminal side of the glutamate residues to be carboxylated. The enzyme may then carboxylate multiple glutamate residues in that area, for example all glutamate residues in the GLA domain, before releasing the substrate. The Factor IX polypeptide for use in the present invention may therefore comprise a motif or site that is recognised by γ-glutamyl carboxylase or by another enzyme capable of gamma carboxylation. This recognition site may be located in the N-terminal region of Factor IX, for example within the 18, 19, 20, 21, 22, 23, 24, 25, 30, 35 or 40 amino acids closest to the N terminal of Factor IX as translated, or to what will be the N terminal of the mature protein. The recognition site may be located on the amino terminal side of the glutamate residues to be carboxylated. For example, in many naturally occurring gamma carboxylated proteins, the γ-glutamyl carboxylase enzyme recognises and binds to a site in the propeptide region. That region is subsequently cleaved from the rest of Factor IX during post-translational processing. The gamma carboxylase recognition site may therefore be absent from the mature protein.

In Factor IX, the site involved in recognition of the γ-glutamyl carboxylase enzyme is defined by residues −18, −17, −15, −15 and −10. A similar recognition site is found in other gamma carboxylated proteins. A phenylalanine at position −16 and alanine at position −10 are well conserved within the propeptides of carboxylase substrates, as are aliphatic residues such as isoleucine, leucine and valine at positions −17 and −15. Leucine, valine or lysine at position −16 may also support carboxylation. It will be appreciated that the process of the invention may equally apply to purification of a polypeptide which comprises a gamma carboxylation recognition site from a known gamma carboxylated protein, such as a gamma carboxylation recognition site from Factor IX, Factor X, Factor VII, or any of the other known gamma carboxylated proteins. For example, a propeptide region from any such protein, which comprises a gamma carboxylation recognition site may be present at the N terminus of the translated polypeptide to allow suitable post-translational processing of the polypeptide by γ-glutamyl carboxylase.

In order for gamma carboxylation of Factor IX to occur, Factor IX is preferably expressed in a cell. Factor IX for use in the invention may be synthesised by expression in such a cell. Preferably, the cell in which Factor IX is expressed includes the necessary cellular machinery to allow for gamma carboxylation of Factor IX. For example, the cell may express γ-glutamyl carboxylase. Preferably the cell in which Factor IX is synthesised has a gamma carboxylase enzyme associated with the rough endoplasmic reticulum. The cell may be cultured in the presence of enzyme cofactors such as vitamin K. Preferably the cell in which Factor IX is synthesised comprises intracellular vitamin K.

The methods of the invention involve the purification of one or more species of Factor IX from other species of Factor IX having different degrees of gamma carboxylation. Where Factor IX can be gamma carboxylated at more than one site, different species of Factor IX may exist in which different numbers of gamma carboxyglutamate amino acid residues are present, or in which gamma carboxyglutamate residues are present at different possible locations within the Factor IX molecule.

For example, some species of Factor IX may be fully gamma carboxylated. That is, gamma carboxylation may have converted glutamate to gamma carboxyglutamate at all residues in Factor IX where this is possible, for example at all Glu residues in the GLA domain. Other species of Factor IX may be partially gamma carboxylated. That is, gamma carboxylation may have converted glutamate to gamma carboxyglutamate at some, but not all residues in Factor IX where this is possible, such as at some, but not all of the Glu residues in the GLA domain.

A variety of different partially gamma decarboxylated species may be identified. These may be classified in various ways. For example, the level of gamma decarboxylation may be defined by which residues in Factor IX are gamma decarboxylated, or may be defined by the total number of gamma carboxyglutamate amino acids present in the polypeptide. The latter classification may mean that a number of structurally different molecular species of Factor IX are considered together based on the total number of gamma carboxyglutamic acid residues that they contain. For example a species of Factor IX in which all but one of the possible gamma carboxyglutamate residues is present may contain multiple different subspecies of Factor IX, in which glutamate is retained at different positions that might have been gamma carboxylated.

Because of the mechanism of action of γ-glutamyl carboxylase, gamma carboxylation generally starts at the Glu residue closest to the gamma carboxylation recognition site and progresses away from the N terminal of Factor IX. Where Factor IX is not fully gamma carboxylated, this is generally because gamma carboxylation is halted, or the enzyme is released from Factor IX, before the furthest Glu residues have been converted. It is generally the Glu residues furthest from the gamma carboxylation binding site or furthest from the N terminus of Factor IX that are not gamma carboxylated in a partially gamma carboxylated Factor IX.

For example, as shown in FIG. 1, human Factor IX includes up to 12 gamma carboxyglutamate residues. The actual number of Gla residues present will vary in different polypeptide molecules depending upon the degree of post translational modification by gamma carboxylation that the molecule has undergone. This means that a sample of human Factor IX may comprise species of Factor IX that are fully gamma decarboxylated, i.e. that have all 12 possible gamma carboxyglutamate residues (#1-12 Gla).

It may also comprise one or more species of Factor IX having 11 of the possible 12 gamma carboxyglutamate residues. Of these, the most likely is the situation where the 11 Glu residues closest to the N terminus of the polypeptide are converted to Gla, but the $12^{th}$ Glu residue, at position 40 as shown in FIG. 1, remains as a Glu. Thus, in this situation, only Glu residues 1 to 11 have been converted to Gla (#1-11 Gla).

It may also comprise one or more species of Factor IX having 10 of the possible 12 gamma carboxyglutamate residues. Of these, the most likely is the situation where the 10 Glu residues closest to the N terminus of the polypeptide are converted to Gla, but the $11^{th}$ and $12^{th}$ Glu residues, at positions 36 and 40 as shown in FIG. 1, remain as Glu. Thus, in this situation, only Glu residues 1 to 10 have been converted to Gla (#1-10 Gla).

It may also comprise one or more species of Factor IX having 9 of the possible 12 gamma carboxyglutamate residues such as #1-9 Gla. It may also comprise one or more species of Factor IX having less than 9, such as 8, 7, 6, 5, 4, 3, 2, 1 or none of the possible 12 gamma carboxyglutamate residues.

The present invention provides methods for the purification of such a species of Factor IX. In particular, a species of Factor IX may be purified in relation to other species of Factor IX in the sample. Thus, a method of the invention may lead to an increase in the relative proportion of a species of interest in the sample of Factor IX. This may be achieved by removing one or more different species of Factor IX from the sample, and thus increasing the proportion of the Factor IX as a whole that is formed from the species of interest. This may be achieved through specific removal of one of more particular species from the sample, by the removal of one or more species that are not the species of interest from the sample, or by removing a fraction of the sample in which the proportion of the species of interest is lower than that in the original sample. Any of these approaches may lead to an overall increase in the proportion of the species of interest. The methods of the invention may thus lead to an increase or decrease in the proportion of a particular species of Factor IX in a sample comprising a mixture of different species of Factor IX.

An increase in the proportion of a Factor IX species may be an increase of up to 5%, up to 10%, up to 20%, up to 30% or more in the proportion of that species in the sample of Factor IX as a whole. A decrease in the proportion of a Factor IX species may be a decrease of up to 5%, up to 10%, up to 20%, up to 30%, up to 50%, up to 70%, up to 90% or more in the proportion of that species in the sample of Factor IX as a whole. A decrease in the proportion of a Factor IX species may be a decrease of up to 5%, up to 10%, up to 20%, up to 30%, up to 50%, up to 70%, up to 90% or more in the amount of that species that is present compared to the amount present in the original sample. A decrease in the proportion of a Factor IX species may be the complete or substantial removal of that species from the sample. For example, a method of the invention may purify a sample of Factor IX by removing all, or substantially all, detectable Factor IX of a particular species from the sample. The amount of such a species remaining in the sample may be less than 10%, less than 5%, less than 2% or less than 1% of the amount present in the original sample.

The purpose of the methods of the invention is thus to allow the relative proportions of the different species in a sample of Factor IX to be altered. Different species may have different properties or different activities. By changing the amount or proportion of such species in a sample of Factor IX, the properties or activity of the sample as a whole may be altered. For example, where different species of Factor IX have different levels of activity, by altering the proportions of different species in order to increase the proportion of species having higher levels of activity and/or by decreasing the proportions of species having lower or no activity, the specific activity of the sample, e.g. the average activity per molecule of Factor IX or the percentage of the maximum possible activity for that amount of Factor IX, may be increased.

For example, it has been found that recombinantly produced human Factor IX (rhFIX) shows a specific activity of approx. 50%. Fractionization of such a sample showed that it contained individual rhFIX species with a predominance of #1-8-, #1-9-, #1-10-#1-11- and #1-12-Gla. It has been found that #1-11- and #1-12-Gla are fully active in a clot assay and in a 2-stage activity assay. The #1-8-, #1-9- and #1-10-Gla species showed decreased activity to approx. 2-5%, 14-22% and 27-36% depending on the assay used.

It can therefore be seen that different species of rhFIX, which vary only in their degree of gamma carboxylation, show differing levels of activity. A sample with a higher proportion of #1-11- and/or #1-12-Gla would be expected to show a higher specific activity than a sample having a lower proportion of those species. A sample with a higher proportion of #1-8- and/or #1-9- and/or #1-10-Gla would be expected to show a lower specific activity than a sample having a lower proportion of those species.

Thus, the overall specific activity of a sample of Factor IX may be altered by altering the proportions of such species within the sample. In this case, it can be predicted that the overall specific activity of a sample of Factor IX may be increased by any one or more of the following:
increasing the proportion of #1-12-Gla in the sample;
increasing the proportion of #1-11-Gla in the sample;
decreasing the proportion of #1-10-Gla in the sample;
decreasing the proportion of #1-9-Gla in the sample;
decreasing the proportion of #1-8-Gla in the sample;
decreasing the proportion of #1-7-Gla in the sample;
decreasing the proportion of #1-6-Gla in the sample;
decreasing the proportion of #1-5-Gla in the sample;
decreasing the proportion of #1-4-Gla in the sample;
decreasing the proportion of #1-3-Gla in the sample;
decreasing the proportion of #1-2-Gla in the sample; and
decreasing the proportion of #1-1-Gla in the sample.

Any one or more of these changes may be selected for when purifying a sample of Factor IX in accordance with the present invention.

A preferred sample of Factor IX will comprise only #1-11-Gla and #1-12-Gla and will lack or substantially lack species having lesser degrees of gamma carboxylation than this, such as #1-10-, #1-9- and #1-8-Gla species.

This approach may be applied to existing compositions of hFIX. It can be seen that the methods described herein may be used to increase the proportion of #1-11-Gla and/or #1-12-Gla in such compositions. The methods described herein may be used to decrease the proportion of less gamma carboxylated species such as #1-10-Gla, #1-9-Gla and #1-8-Gla in such formulations. This would be expected to improve the specific activity of the hFIX in such a formulation.

A similar approach may be used in relation to other Gla-containing polypeptides. For example, Factor VII and Factor X may include up to 11 Gla residues.

The invention thus provides methods which allow a species of Factor IX to be purified from other species of Factor IX, wherein the species differ in the extent to which they are gamma carboxylated, or in the number of Gla residues in their amino acid sequence.

The method of the invention is based on immunoaffinity chromatography. The invention relates in particular to methods where Factor IX is bound to an immunoaffinity material containing a GLA-directed antibody coupled to a bead and elution of Factor IX from the immunoaffinity material is performed using a buffer.

By immunoaffinity material is meant a GLA-directed antibody coupled to a chromatography resin. The immunoaffinity material therefore has an antibody or antibody derived binding motif for gamma-carboxylated residues. The antibody may be attaching to a solid phase. The solid phase may be, for example, a purification column, particles or beads, a membrane or a filter. Commercially available coupling materials that may be used as described herein include, for example, CNBr Sepharose™ Fast Flow, NHS Sepharose™ Fast Flow, Epoxy Sepharose™ 6B, Thiol Sepharose™ Fast Flow, EAH Sepharose™ Fast Flow, Epoxy Poros® EP, Aldehyde Poros® AL, Epoxy Poros® EP and Hydroxylated Poros® OH.

For example, purification of Factor IX in accordance with the invention will typically comprise a Sepharose FF affinity material (i.e. CNBr Sepharose 4 FF) coupled with the binding moiety for Gla (i.e. FIX antibody 3F14A3B6).

It will be appreciated that the invention is based on an affinity chromatographic procedure, which principally means using a ligand interaction for purification of a target protein. Thus. the term affinity refers to but not limited to a specific molecular interaction between the ligand and the target protein. The interaction may be dependent on a specific folding state of the protein or ligand. The ligand may be immobilized to a resin as described above. The resin used comprises a binding moiety for Gla which is immobilized to a suitable chromatographic bead. In one embodiment, the binding moiety for Gla comprises a Gla directed antibody. In this embodiment, the epitope recognized by the antibody is a folded Gla domain, which has surprisingly been shown to occur only for FIX species with #1-8-Gla or higher. It will be appreciated that by ensuring that the total concentration of Factor IX within said sample exceeds the binding ability of the immunoaffinity chromatography material ensures that the immunoaffinity column is overloaded. For example, the concept of overloading means that the amount of FIX loaded onto the column is higher than the FIX capacity of the column in question.

In one embodiment, the binding ability of the immunoaffinity chromatography material is exceeded by greater than any one of 100, 105, 110, 115, 120, 125, 130, 140, 150, 200, 250, 500, 750 or 1000%, in particular greater than 120% (i.e. 122%) or greater than 150% (i.e 170%) or greater than 250% (i.e. 334%). In a further embodiment, the binding ability of the immunoaffinity chromatography material is exceeded by greater than 100% but is lower than 500%, i.e. lower than any one of 450, 400, 350, 300, 250, 200 or 150% (or any ranges therebetween, such as 100-400%, 100-200% or 100-150%). According to an alternative aspect of the invention, there is provided a method for purifying a polypeptide having a desired content of gamma-carboxyglutamic acid from a sample comprising a mixture of species of said polypeptide having different contents of gamma-carboxyglutamic acid, said method comprising the steps of:
(a) loading said polypeptide sample onto an immunoaffinity chromatography material coupled to a binding moiety for gamma-carboxyglutamic acid;
(b) eluting said polypeptide; and
(c) selecting a fraction obtained from said elution wherein the polypeptides in the fraction have the desired content of gamma-carboxyglutamic acids; characterised in that the total concentration of polypeptide within said sample exceeds the binding ability of the immunoaffinity chromatography material by between 100 and 400%. In one embodiment of the alternative aspect of the invention, the polypeptide is Factor IX, VII or X, such as Factor IX. In one embodiment of the alternative aspect of the invention, the binding ability of the immunoaffinity chromatography material is lower than any one of 350, 300, 250, 200 or 150% (or any ranges therebetween, such as 100-200% or 100-150%).

An additional advantage of the immunoaffinity chromatographic aspect of the invention is the consistent delivery of very pure FIX with a very low amount of activated FIX (FIXa).

Examples of Gla-directed antibodies which may be used in the invention include those described in Liebman H A (1993) Eur. J. Biochem. 212: 339-345, Liebman H A et al (1987) J. Biol. Chem. 262: 7605-7612 and Gillis S et al (1997) Protein Sci. 6:185-96. In one embodiment, the Gla-directed antibody is 3F14A3B6. The name 3F14A3B6 refers to the hybridoma clone from which the monoclonal antibody was produced. The 3F14A3B6 hybridoma clone producing the FIX Gla-directed monoclonal antibody was identified by screening a hybridomas pool established from splenocytes obtained from FIX immunized mice fused with an immortalized mouse myeloma cell line. Hybridoma cells were harvested and total RNA was isolated and used to prepare cDNA using commercially available RNA and cDNA preparation kits. Thus, the cloned 3F14A3B6-LC and 3F14A3B6-HC cDNA sequences were obtained. From the sequencing data it was established that the anti-FIX antibody is a murine IgG1 antibody. The amino acid sequences corresponding to the cDNA sequences of 3F14A3B6-HC and 3F14A3B6-LC are shown in SEQ ID NOS: 1 and 2, respectively. Based on the sequences, standard transient and stable recombinant expressions were performed. The antibody was purified using conventional Protein-A based affinity chromatography and prepared for resin coupling by formulation in relevant buffers such as 0.1 M $Na_2CO_3$, 0.5 M NaCl, pH 8.3.

The effectiveness of the overloading principal will depend on the specific epitope in the Gla domain recognized by the antibody or antibody derivative, such as for example a Fab or a scFv fragment, used in the invention. A preferred antibody used in the invention is an antibody, which is sensitive to folding of the Gla domain in the presence of calcium, magnesium or other divalent cations and/or an antibody recognizing an epitope containing specific Gla residues. An example may be FIX, in which the epitope of the antibody recognises Gla#1, Gla#2, Gla#3, Gla#4, Gla#5, Gla#6, Gla#7, Gla#8, Gla#9, Gla#10, Gla#11 or Gla#12, or an overlap with any of the mentioned Gla residues and/or other nabouring non-Gla residues. Specifically for coagulation factors, calcium-dependent antibodies directed towards the Gla domain can generally be divided into two categories: (I) those with an absolute requirement for calcium, and (II) those where calcium can be substituted for magnesium or other divalent cations without compromising binding (Liebman, H. A. et al (1987) JBC 262: 7605-7612). Structural studies have shown that class I antibodies binds to the N-terminal part of the Gla-domain, while class II binds to the C-terminal part. Localization of the epitopes to different regions of the Gla domain has been rationalized by NMR spectroscopy demonstrating that calcium is capable of inducing folding of the entire Gla domain, whereas magnesium only supports folding of the distal part close to the EGF1 domain and leaves the N-terminal w-loop unstructured (Freedman, S. J. et al (1996) JBC 271: 16227-16236; Freedman, S. J. et al (1995) JBC 270: 7980-7987; Huang, M. et al (2004) JBC 279: 14338-14346).

When the principal of overloading is utilized for the antibody 3F14A3B6, the FIX Gla species #1-8-#1-10 can be displaced by the FIX Gla species #1-11-#1-12. When the column is finally eluted after appropriate wash steps, the total amount of the low FIX Gla species #1-8-#1-10 has been reduced significantly compared with procedures where the column capacity has not been exceeded. In one embodiment, the Gla-directed antibody (i.e. 3F14A3B6) is immobilised on a sepharose bead, such as a pre-activated sepharose bead, in particular CNBr-Sepharose 4 FF.

A conventional immunoaffinity chromatography purification process usually consists of one or more steps selected from: equilibration of the immunoaffinity material, application or loading of a sample, one or more washing steps, elution and regeneration of the immunoaffinity material. Standard methods for affinity chromatography may be found in, for example, Remington's Pharmaceutical Sciences.

The immunoaffinity resin is preferably equilibrated prior to loading the Factor IX sample. The purpose of this equilibration step is to adjust the conditions at the immunoaffinity material to more closely resemble those to be used in the subsequent steps of the method. To avoid changes in the composition of the mobile phase during the chromatography, the immunoaffinity material should be equilibrated to the pH and ionic composition (e.g. conductivity, buffer composition) of the starting buffer. For example, the ionic strength (e.g. conductivity, pH) of the equilibration buffer may be selected to be as similar as possible to the ionic strength of buffers to be used in later steps of the method, such as the buffer used to load the polypeptide and/or the wash buffer(s).

The immunoaffinity material may therefore be equilibrated using a buffer that is closely based on the buffers or formulations to be used in the subsequent steps. For example, the same buffer may be used for equilibration of the immunoaffinity material and for loading the sample. The same buffer may be used for equilibration of the immunoaffinity material and for washing the immunoaffinity material after the sample has been loaded. The equilibration buffer may have the same pH as the loading formulation and/or the wash buffer. The equilibration buffer may have the same conductivity as the loading formulation and/or the wash buffer. The equilibration buffer may use the same buffering substance as the loading formulation and/or the wash buffer. The equilibration buffer may have the same buffering substance concentration as the loading formulation and/or the wash buffer. The equilibration buffer may comprise additional components also present in the loading formulation and/or the wash buffer, such as detergents.

The pH of the equilibration buffer may be determined depending on the particular polypeptide to be purified. For example, for a number of polypeptides such as Factor IX, a pH of 9.0 or higher is not optimal, since autoactivation and/or degradation of the polypeptide may be observed at these pH values.

An equilibration buffer for use in the present invention may be formulated at, for example a pH of from about 5.0 to about 8.5, such as from pH 5.0 to pH 8.5. The pH of an equilibration buffer may be greater than about 5.0, greater than about 5.5, greater than about 6.0, greater than about 6.5, greater than about 7.0, greater than about 7.5 or greater than about 8.0. The pH of the equilibration buffer may be less than about 8.5, less than about 8.0, less than about 7.5, less than about 7.0, less than about 6.5, less than about 6.0 or less than about 5.5. Any combination of such end points may be combined. For example the pH of the equilibration buffer may be greater than about 7.0 and less than about 8.5. The pH may be, for example, about pH 7.0, 7.5, 8.0 or 8.5, such as about 7.5.

These pH values may be suitable for the equilibration of immunoaffinity materials for the purification of polypeptides as described herein, such as Factor IX, Factor VII or Factor X.

Suitable components for an equilibration buffer may include a buffering substance, e.g. Tris, phosphate, MES, Hepes or carbonate. Such a buffering substance may be used to maintain the equilibration buffer at a pH as defined above. In one embodiment, the same buffering substance and buffering substance concentration are used throughout the immunoaffinity chromatography procedure. For example, the equilibration buffer, wash buffer(s) and elution buffer may all comprise the same buffering substance at the same buffering substance concentration. The buffering substance concentration should be sufficient to maintain buffering capacity and constant pH during the immunoaffinity procedure. For example, the buffering substance and buffering substance concentration may be selected to maintain a stable pH and buffering capacity during application of the sample and during elution. A suitable buffering substance concentration may be, for example, between 5 mM and 50 mM, such as between 10 mM and 40 mM. A suitable buffering substance concentration may be, for example, 5 mM, 10 mM, 15 mM, 20 mM or 25 mM, such as 20 mM.

An equilibration buffer may comprise one or more additional components. An equilibration buffer may comprise an additive such as ethylene glycol, ethanol, urea or a detergent used to increase solubility of a protein. Non-ionic detergents such as Tween 80, Tween 20 or Triton X100 may be used in a concentration of, for example, less than 1%, less than 0.5%, less than 0.1% or less than 0.01%. A non-buffering salt, such as NaCl may be used to adjust the ionic strength of the buffer.

In one embodiment the equilibration buffer additionally comprises calcium ions, such as calcium chloride. In one embodiment, the calcium ions are present in a concentration of greater than 0.5 mM (e.g. greater than 0.5, 1.0, 1.5, or 2.0 mM calcium chloride, such as 3.0, 5.0, 8.0 or 10.0 mM calcium chloride, in particular 2 or 5 mM calcium chloride). In other embodiments, the calcium ions are present in the ranges of 0.5-10 mM, 1-8 mM, 1-5, and 2-5 mM. As demonstrated by the data presented herein in Example 2, these data indicate that the species #1-8-#1-9 display a highly decreased cooperativity and increased calcium dependence compared to the species #1-11-#1-12. These data can be combined with the overloading principal in a way such that overloading yields an even better Gla profile.

A sample comprising Factor IX is loaded onto the immunoaffinity material. This is achieved by exposing the sample to the immunoaffinity material under appropriate conditions (such as presence of calcium, conductivity and/or pH) such that Factor IX is immobilised in or on the immunoaffinity material. This immobilisation or binding is achieved by the calcium specific folding of GLA domain of Factor IX and the GLA-specific antibody 3F14A3B6. Such binding occurs only when the GLA domain is sufficiently folded.

The sample to be purified in a method of the invention may be any sample comprising Factor IX as described above. Preferably the sample comprises more than one different species of the same polypeptide wherein the species vary in the degree and/or location of their gamma carboxylation.

As mentioned above, Factor IX may be obtained using any routine procedure. For example, Factor IX may be obtained from an in vivo source, such as from an animal, or may be produced in vitro, for example in a tissue or cell. The Factor IX may be recombinantly produced, for example by inducing the expression of Factor IX in a cell. For example, Factor IX may be produced in a host cell that has been transformed or transfected with a polynucleotide that encodes, and is capable of expressing, Factor IX. Such a host cell may be cultured under conditions that allow the expression of Factor IX. Factor IX may then be recovered from the culture medium or from the host cells themselves.

Factor IX may be purified before being applied to the immunoaffinity resin. For example, Factor IX may be subjected to one or more purification steps such as precipitation, immunoprecipitation, isoelectric focusing, filtration, centrifugation or chromatography such as anion or cation chromatography.

For example, the described invention of purifying a Gla domain containing protein/polypeptide using an immunoaffinity-based overloading method may be combined with a second step in which the Gla species are further separated/purified using an anion chromatography based method. One such method could for example be a method utilizing ammonium acetate to separate further protein/polypeptide Gla species, which for example were not fully separated using an immunoaffinity-based overloading method. A specific example may be FIX Gla species purified first using an immunoaffinity-based overloading method and second using an anion chromatography method, combined with an eluent containing for example ammonium acetate, ammonium chloride, sodium acetate or sodium chloride, in which the content of low Gla species, such as for example Gla#1-12, Gla#2-12, Gla#3-12, Gla#4-12, Gla#5-12, Gla#6-12, Gla#7-12, Gla#8-12 and Gla#9-12, are separated even further from high Gla species, such as for example Gla#10-12, Gla#11-12 or Gla#12-12, when compared to the Gla profile obtained from each of the individual methods alone.

Such purification may be used to remove, partially or totally, one or more contaminants from the sample and thereby increase the degree of purity of the Factor IX. The contaminant may be any molecule that is not Factor IX. For example, the contaminant may be a different polypeptide, a nucleic acid or an endotoxin. The contaminant may be a variant of Factor IX, such as a truncated or extended polypeptide, a deamidated form of Factor IX, an incorrectly folded polypeptide or a form of the polypeptide having undesired glycosylation. The contaminant may be a molecule that might interfere with the immunoaffinity chromatography.

Preferably Factor IX is at least 75% pure, more preferably at least 80%, at least 90% or more. Most preferably Factor IX is at least 90% pure, such as at least 95%, at least 97% or at least 99% pure. Purity is intended to refer to the proportion of the total dry weight that is made up of Factor IX. The sample may comprise less than 25% by weight of contaminants as described above, such as less than 25% by weight of proteins other than Factor IX, more preferably less than 20%, less than 10%, less than 5%, less than 3% or less than 1%. The sample may be a pure or substantially pure sample of Factor IX. The sample may be an isolated or substantially isolated sample of Factor IX.

Such a sample of Factor IX may be applied to immunoaffinity material in a form obtained directly from the Factor IX synthesis, such as in the form of a sample from the culture medium of cells that recombinantly produce Factor IX or a sample of lysed cells that expressed Factor IX. A sample of Factor IX may be applied to the immunoaffinity material in a purified or partly purified form as described herein. A sample as described herein may be further formulated before application to the immunoaffinity material. For example, where the Factor IX (or purified Factor IX) is provided in a solid form, it may be formulated in a liquid composition for application to the immunoaffinity material. For example, it may be formulated in water, a buffer or another solvent. Preferably, the liquid composition is aqueous. Where the Factor IX or purified Factor IX is provided in a liquid or aqueous form, or where a solid Factor IX sample has been formulated in a liquid form as described above, the formulation of the sample may be adjusted before it is applied to the immunoaffinity material.

For example, the conductivity and/or the pH of the sample or formulated sample, e.g. with added calcium, may be adjusted using routine methods. The pH of the sample may be adjusted to be the same as, or substantially the same as, that of the buffers used for equilibration of the immunoaffinity material and/or washing of the immunoaffinity material. The conductivity of the sample may be adjusted to be the same as, or substantially the same as, that of the buffers used for equilibration of the immunoaffinity material and/or washing of the immunoaffinity material. The sample may be formulated with a buffering substance, such as any of the buffering substances discussed above in relation to the composition of the equilibration buffer. The sample may be formulated in the same buffer used for equilibration of the immunoaffinity material and/or washing of the immunoaffinity material. The sample may be formulated in the same buffering substance and/or the same buffering substance concentration and/or the same pH and/or the same conductivity as the buffer used for equilibration of the immunoaffinity material and/or washing of the immunoaffinity material. In one embodiment, Factor IX is formulated for application to an immunoaffinity material by adding it to a calcium containing buffer identical to the equilibration buffer that is being used.

Factor IX is then loaded onto the immunoaffinity material by passing the relevant formulation of Factor IX over or through the immunoaffinity material under conditions that allow for overloading of Factor IX to the immunoaffinity material. Such methods are routine in the art. For example, the capacity of the column is measured based on active Factor IX and is assigned a given value in g/L. The sample is then loaded at a value which exceeds the capacity in g/L by more than 100% as hereinbefore defined.

Once the Factor IX is loaded onto the immunoaffinity column, the column may be subjected to one or more washes. Washing is achieved by passing an appropriate solution through or over the immunoaffinity material. The purpose of such washes may include to remove any Factor IX or other components that are not bound to the immunoaffinity material; to remove any Factor IX or other components that are only weakly bound to the immunoaffinity material; to remove impurities that bind to the immunoaffinity material with a lower affinity than Factor IX.

In one embodiment, after loading of Factor IX onto the immunoaffinity material, the immunoaffinity material is washed with a buffer in order to remove any unbound Factor IX, contaminants or impurities. For example, the wash buffer may be identical to, or substantially identical to, the buffer in which Factor IX was formulated for loading onto the immunoaffinity material. The wash buffer may be identical to, or substantially identical to, the equilibration buffer. For example, a wash may be carried out using the same buffer as the equilibration buffer or the same buffer used to formulate Factor IX. A wash may be carried out using a buffer having the same or substantially the same pH and/or the same or substantially the same conductivity as the equilibration buffer or the buffer used to formulate Factor IX. A wash may be carried out using a buffer that comprises the same buffering substance at the same or substantially the same concentration as that used in the equilibration buffer or for the formulation of Factor IX.

Other washes may alternatively or additionally be carried out using buffers that are different to the equilibration buffer. For example, it may be possible to remove contaminants from the immunoaffinity material that bind to the immunoaffinity material less strongly than Factor IX. Such contaminants will be released from the immunoaffinity material more easily than Factor IX. For example, the immunoaffinity material may be washed with a buffer having a greater conductivity or ionic strength than the equilibration buffer and/or the formulation in which Factor IX was loaded. By increasing the ionic strength of the buffer, elution of components from the immunoaffinity material may be achieved. Preferably the wash buffer is selected, or is used in a sufficiently small volume such that substantially no Factor IX is eluted from the immunoaffinity material.

Buffers for washing may be selected by a skilled artisan depending upon the nature of the particular sample and polypeptide of interest. For example, buffers may be selected having a particular pH or conductivity to allow for the removal of particular polypeptides or impurities that will bind to the resin less strongly than the polypeptide of interest. Such buffers may be selected and their use optimised by simple routine experiments, for example by monitoring the composition of the solution removed from the column.

The pH of a wash buffer may be determined depending on the particular polypeptide to be purified. For example, for a number of polypeptides, such as Factor IX, a pH of 9.0 or higher is not optimal, since autoactivation and/or degradation of the polypeptide may be observed at these pH values.

A wash buffer suitable for use in the present invention may be formulated at, for example a pH of from about 5.0 to about 8.5, such as from pH 5.0 to pH 8.5. The pH of a wash buffer may be greater than about 5.0, greater than about 5.5, greater than about 6.0, greater than about 6.5, greater than about 7.0, greater than about 7.5 or greater than about 8.0. The pH of the wash buffer may be less than about 8.5, less than about 8.0, less than about 7.5, less than about 7.0, less than about 6.5, less than about 6.0 or less than about 5.5. Any combination of such end points may be combined. For example the pH of the wash buffer may be greater than about 7.0 and less than about 8.5. The pH may be, for example, about pH 7.0, 7.5, 8.0 or 8.5, such as 7.5.

These pH values may be suitable for the washing of immunoaffinity materials for the purification of polypeptides as described herein, such as Factor IX, Factor VII or Factor X.

Suitable components for a wash buffer may include a buffering substance, e.g. Tris, phosphate, MES, Hepes or carbonate. Such a buffering substance may be used to maintain the wash buffer at a pH as defined above. A suitable buffering substance concentration may be, for example, between 5 mM and 50 mM, such as between 10 mM and 40 mM. A suitable buffering substance concentration may be, for example, 5 mM, 10 mM, 15 mM, 20 mM or 25 mM, such as 20 mM.

A wash buffer may comprise one or more additional components. A wash buffer may comprise an additive such as ethylene glycol, ethanol, urea or a detergent used to increase solubility of a protein. Non-ionic detergents such as Tween 80, Tween 20 or Triton X100 may be used in a concentration of, for example, less than 1%, less than 0.5%, less than 0.1% or less than 0.01%. A non-buffering salt, such as NaCl may be used to adjust the ionic strength of the buffer.

In one embodiment the wash buffer additionally comprises calcium ions, such as calcium chloride, or similar divalent ions, e.g. magnesium ions, strontium ions, beryllium ions, zink ions, nickel ions, and cupper ions. In one embodiment, the calcium ions are present in a concentration of greater than 1 mM (i.e. greater than 1 mM calcium chloride, such as 2 mM calcium chloride, in particular 1.5 mM calcium chloride). As demonstrated by the data presented herein in Example 2, these data indicate that the species #1-8-#1-9 display a highly decreased cooperativity and increased calcium dependence compared to the species #1-11-#1-12. These data can be combined with the overloading principal in a way such that overloading yields an even better Gla profile.

To elute a molecule from an immunoaffinity material is meant to remove the molecule from the immunoaffinity material. This is generally achieved by interfering with interaction of the ligand of the affinity material and the bound target molecule by adding and/or removing buffer additives, changing conductivity, pH and/or temperature. The binding strength of the molecule for the affinity material thereby decreases and it detaches. Elution from an immunoaffinity material may also be achieved in some cases by using a molecule that alters the conformation of the target protein, e.g. Factor IX, thus reducing the binding strength and causing the target molecule to be released from the immunoaffinity material. This additive could be a chelating agent, for example EDTA, EGTA or citrate, which binds calcium ions strongly leading to dissociation of calcium ions from Factor IX. Consequently, the GLA domain of Factor IX will unfold, resulting in an obstructed ligand binding for Factor IX when specifically the binding requires a folded GLA domain, e.g. the antibody ligand 3F14A3B6.

The pH of the elution buffer may be determined depending on the particular polypeptide to be purified. For example, for a number of polypeptides, such as Factor IX, a pH of 9.0 or higher is not optimal, since autoactivation and/or degradation of the polypeptide may be observed at these pH values.

An elution buffer suitable for use in the present invention may be formulated at, for example a pH of from about 5.0 to about 8.5, such as from pH 5.0 to pH 8.5. The pH of an elution buffer may be greater than about 5.0, greater than about 5.5, greater than about 6.0, greater than about 6.5, greater than about 7.0, greater than about 7.5 or greater than about 8.0. The pH of the elution buffer may be less than about 8.5, less than about 8.0, less than about 7.5, less than about 7.0, less than about 6.5, less than about 6.0 or less than about 5.5. Any combination of such end points may be combined. For example the pH of the elution buffer may be greater than about 7.0 and less than about 8.5. The pH may be, for example, about pH 7.0, 7.5, 8.0 or 8.5, such as 7.5

These pH values may be suitable for the elution of immunoaffinity materials for the purification of polypeptides as described herein, such as Factor IX, Factor VII or Factor X.

Suitable components for an elution buffer may include a buffering substance, e.g. Tris, phosphate, MES, Hepes or carbonate. For an immunoaffinity chromatography method, a positive buffering ion such as Tris is preferred. Such a buffering substance may be used to maintain the elution buffer at a pH as defined above. A suitable buffering substance concentration may be, for example, between 5 mM and 50 mM, such as between 10 mM and 40 mM. A suitable buffering substance concentration may be, for example, 5 mM, 10 mM, 15 mM, 20 mM or 25 mM, such as 20 mM.

An elution buffer may comprise one or more additional components. An elution buffer may comprise an additive such as ethylene glycol, ethanol, urea or a detergent used to increase solubility of a protein. Non-ionic detergents such as Tween 80, Tween 20 or Triton X100 may be used in a concentration of, for example, less than 1%, less than 0.5%, less than 0.1% or less than 0.01%. A non-buffering salt, such as NaCl may be used to adjust the ionic strength of the buffer. As described above, the additive could also be a chelating agent, for example EDTA, EGTA or Citrate, which binds and releases Calcium from Factor IX, consequently leading to unfolding of the GLA domain of Factor IX. Preferably, the concentration of the chelating agent should be equal or above the concentration of calcium in the aqueous solution, for example equilibration buffer, wash buffer or cell supernatant, present in or on the immunoaffinity material prior to elution. If the chelating agent possesses more than one calcium binding site, the concentration of the chelating agent should reflect the stochiometric concentration rather than the absolute concentration.

For use in accordance with the present invention, the elution buffer will preferably comprise one or more additional salts, such as EDTA, EGTA or citrate. In one embodiment, the one or more salts may be present in the elution buffer at a concentration of between 10 mM and 100 mM, such as at least 10 mM, at least 20 mM, at least 25 mM, at least 30 mM, at least 40 mM or at least 50 mM.

In one embodiment the elution buffer has the same composition as a wash buffer and/or the equilibration buffer except that the elution buffer additionally comprises one or more salt and no calcium or other divalent ions. A preferred salt is EDTA. Thus, the elution buffer may have any composition described herein for a wash buffer or equilibration buffer, but may additionally comprise EDTA and no calcium or other divalent ions.

In one embodiment, the equilibration buffer and wash buffer are identical and the elution buffer differs from them only in that the elution buffer also comprises EDTA and no calcium or other divalent ions.

Elution may be performed using an isocratic or linear gradient of the chelating agent, such as an isocratic or linear gradient of EDTA. Preferably, elution is performed using an isocratic gradient of EDTA. Elution may be performed using a step-wise change in the concentration of the EDTA in the buffer. Elution may be achieved by any combination of these elution approaches. For example, isocratic elution at a given concentration of EDTA may be followed by an increase in concentration of EDTA either in the form of a gradient or one or more steps.

In any such elution method, different components will be released from the immunoaffinity material at different times, depending upon the strength of their binding. Components that bind less strongly will tend to be released at earlier or a lower EDTA concentration. Components that bind more strongly will tend to be retained on the immunoaffinity material for longer or at a higher EDTA concentration. The eluant that has passed across or through the immunoaffinity material may be monitored to identify when particular components are eluted. The eluant may be pooled at different time points and each pool analysed to determine which components are present in which pools. Particular pools may then be selected that have the desired formulation, for example increased concentrations of particular Factor IX species or decreased concentrations of other Factor IX species.

Isocratic elution as described herein uses a fixed or steady concentration of the chelating agent. An elution buffer is used which comprises that concentration of the chelating agent, such as any of the concentrations discussed above. The elution buffer is passed across or through the immunoaffinity material and the eluant is monitored to identify when elution occurs. Using isocratic elution, components having lower binding affinity for the immunoaffinity material will be released earlier, when a smaller volume of elution buffer has been used, than components having a higher binding affinity, which may require greater volumes of elution buffer to be passed across or through the immunoaffinity material. By selecting particular pools or batches of eluant obtained at different time periods, samples that have different compositions of Factor IX species may be obtained.

Gradient elution may be achieved by increasing the concentration of the chelating agent, e.g. EDTA, in the buffer up to a final maximum concentration, such as a concentration as discussed above. For example a linear gradient may use from 0% to 100% of the final concentration of the chelating agent, e.g. EDTA. This gradient may be applied to the immunoaffinity material over a period of time, such as over 10, 20, 30 40, 50, 70, 100, 150 or more column volumes. Using such gradient elution, components having lower binding affinity for the immunoaffinity material will be released earlier, at a lower concentration of the chelating agent, e.g. EDTA, than components having a higher binding affinity, which may require a higher concentration of the chelating agent for elution to occur. By selecting particular pools or batches of eluant obtained at different time periods, samples that have different compositions of Factor IX species may be obtained.

Rather than using a gradual gradient to increase the concentration of the salt, a stepwise increase may be used. That is, the concentration of the EDTA may be increased to a final maximum concentration in one or more discrete steps. This may be used to mirror the effects of a gradient elution, wherein different components are released at different concentrations and thus different steps. Stepwise elution may alternatively be combined with isocratic elution. For example, a stepped increase in salt concentration may be maintained for a number of column volumes of the elution buffer, such that isocratic elution at that concentration is allowed to occur, with different components being eluted as increasing volumes of the buffer are used. Subsequent additional steps in salt concentration may also be used.

EXAMPLES

Example 1: Investigation of Calcium Dependence of Different Gamma-Carboxylated Species of FIX to the Gla-Directed Antibody 3F14A3B6

Figure 2:
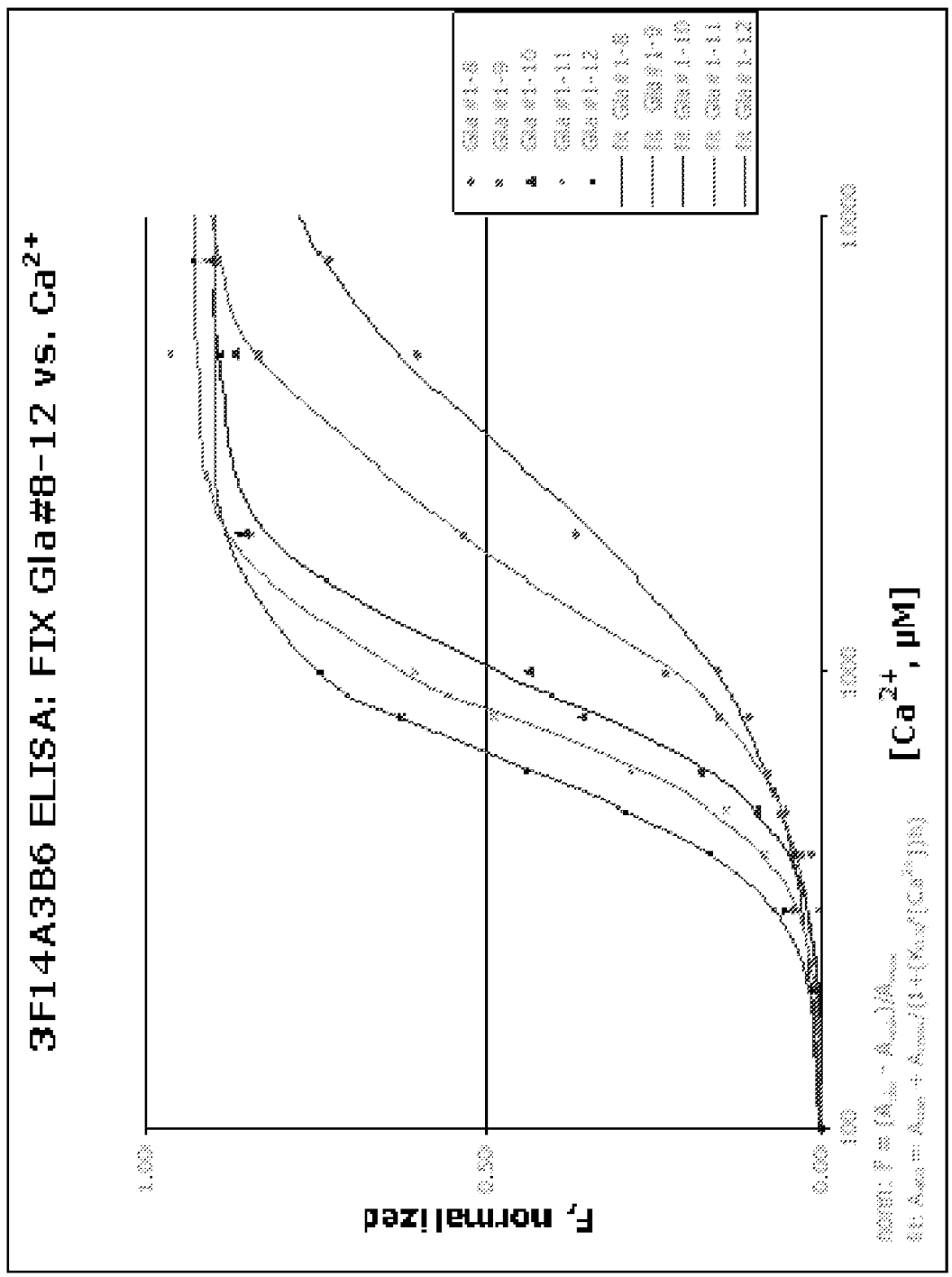
FIG. 2 shows the calcium dependent binding of FIX Gla#1-8-#1-12 to the Gla-directed mAB 3F14A3B6 as evaluated in an ELISA assay described in Example 1.

The calcium dependence of each of the FIX Gla species #1-8-#1-12 to the antibody 3F14A3B6 has been addressed, the results of which can be seen in FIG. 2 and the table below:

|  | Gla#1-8 | Gla#1-9 | Gla#1-10 | Gla#1-11 | Gla#1-12 |
|---|---|---|---|---|---|
| $K_{0.5}$* (µM) | 2891 ± 131 | 1724 ± 12 | 981 ± 29 | 805 ± 5 | 653 ± 40 |
| h** | 1.50 ± 0.00 | 2.15 ± 0.02 | 3.26 ± 0.09 | 3.23 ± 0.01 | 3.2 ± 0.2 |

*$K_{0.5}$ is the calcium concentration resulting in half maximum binding to 3F14A3B6.
**h is the Hill coefficient, which describes whether binding of calcium is cooperative. h > 1 tells that cooperative binding is present, while h = 1 tells that no cooperativity is present.

These data indicate that the species #1-8-#1-9 display a highly decreased cooperativity and increased calcium dependence compared to the species #1-11-#1-12. The FIX Gla specie #1-10 shows intermediate calcium dependence. These data can be combined with the overloading principal in a way such that overloading yields an even better Gla profile.

Example 2: Purification and Analysis of Different Gamma-Carboxylated Species of FIX when Subjected to Immunochromatography with the Gla-Directed Antibody 3F14A3B6 and Column Overloading Application Culture supernatant is added 350 mM NaCl and 1.5 mM $CaCl_2$. NaCl is to be added before the $CaCl_2$ in order to avoid formation of non-soluble Ca-phosphate. If harvest has been thawed, the application sample is filtered at 0.45 μm before loading.

Gel

CNBr Sepharose 4 FF coupled with 2.5 mg 3F14A3B6/ml resin (GE Healthcare).

Column Treatment

The column is packed in a suitable aqua's solvent e.g. the equilibration buffer. After Storage, perform Wash 2 before proceeding to Equilibration.

Parameters

Bed height: ≥5 cm
Temperature: 2-10° C.
Flow: 15 (12-18 CV/h)
Max. pressure: ≤0.1 MPa 1 bar)
Capacity: 0.3 g/L measured as active FIX
Load: 0.36 (120% of capacity) g/L measured as active FIX Buffers A1: 20 mM Tris, 1.5 mM $CaCl_2$, pH 7.5
A2: 20 mM Tris, 1.5 mM $CaCl_2$, 0.5% triton x-100, pH 7.5
A3: 20 mM Tris, 2 M NaCl, 1.5 mM $CaCl_2$, pH 7.5
A4: 20 mM Tris, 20 mM EDTA, 50 mM NaCl, pH 7.5
A5 20 mM Tris, pH 9.0, 4.0 M NaCl, 0.01% (v/v) Triton-X 100
A6: 20 mM NaCitrate, pH 5.5, 4.0 M NaCl, 0.01% (v/v) Triton-X 100

Tris containing solvents are pH adjusted with 4 M HCl

Column Operation

Equilibration: 5 CV 82.5% A1+17.5% A3 (c.t. 20 mM Tris, 350 mM NaCl, 1.5 mM $CaCl_2$, pH 7.5)
Application: As stated, 120% of capacity as stated.
Wash 1: 3 CV 82.5% A1+17.5% A3 (c.t. 20 mM Tris, 350 mM NaCl, 1.5 mM $CaCl_2$, pH 7.5)
Wash 2: 3 CV A3
Wash 3: 2 CV A2 (flow 2 CV/h—contact time 1 h)
Wash 4: 2 CV 97.5% A1+2.5% A3 (c.t. 20 mM Tris, 50 mM NaCl, 1.5 mM $CaCl_2$, pH 7.5)
Elution: 10 CV A4 (Isocratic)
Regeneration 1: 5 CV A5
Regeneration 2: 5 CV A6
Storage: A7 (when stores less than 24 h A1 can be used. A7 is washed out with A3 prior to equilibration)
Product Collection
Start collection: $A_{280} \geq 0.05$
Stop collection: $A_{280} \geq 0.25$ or after 2 CV

EXAMPLES

Some examples of column overloading are shown hereunder. The best mode procedure described in this paragraph was used throughout, except that the application was added 2 mM $CaCl_2$ rather than 1.5 mM.

An IEX-HPLC method was used for the analyses of Gla content performed on an Agilent HPLC system (method is shown in short hereunder). The Gla content analyses based on the HPLC method correlated with Gla content determinations based on N-terminal sequencing and basic hydrolysis analyses.

A MiniQ PC3.2/3 column was used (GE Healthcare cat. no 17-0686-01) at a flow rate of 0.18 ml/min.

The buffers used in this system were:
A-buffer: 2 0 mM Tris, pH 9.0
B-buffer: 20 mM Tris, pH 9.0, 1.5 M Ammonium acetate The following signals were measured
UV280
Fluorescence signal, e.g. ex: 280 nm/em: 340 nm.

The HPLC procedure was the following:

| 0-5 min. | 0-30% B |
| 5-55 min. | 30-55% B |
| 55-65 min. | 55-100% B |

Figure 3A:
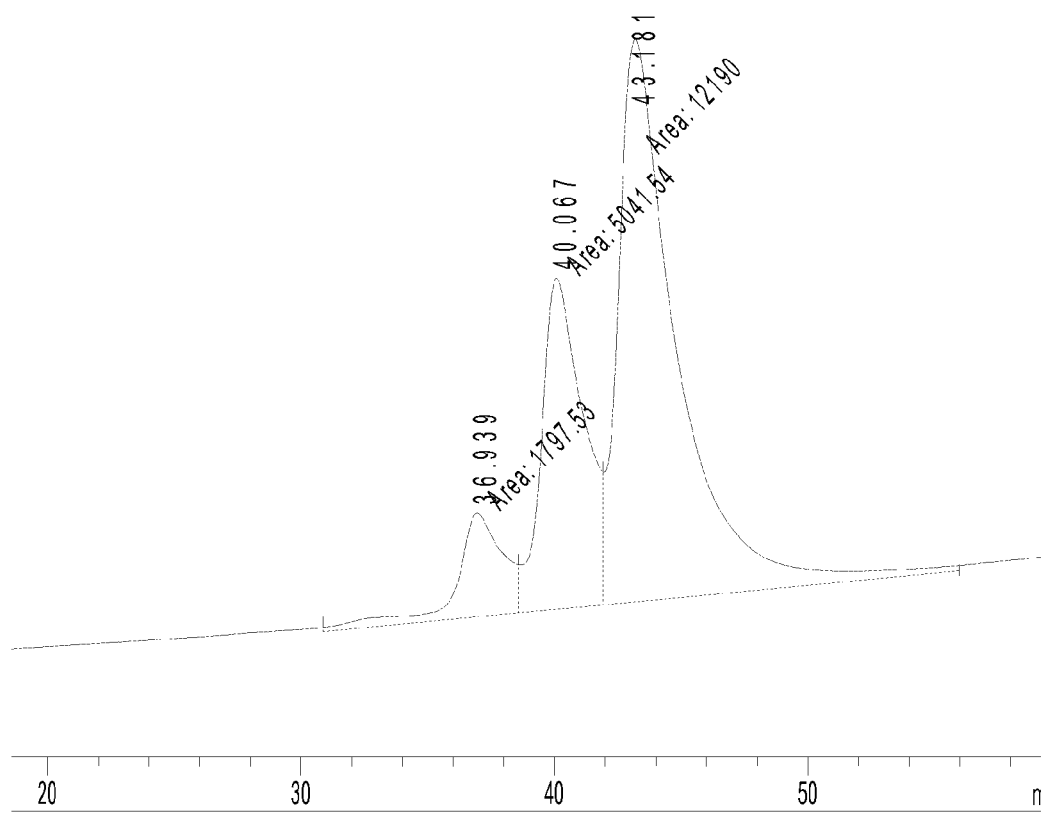
FIG. 3 shows the chromatograms obtained from immunoaffinity chromatography of a sample of FIX as described in Example 2.
Figure 3B:
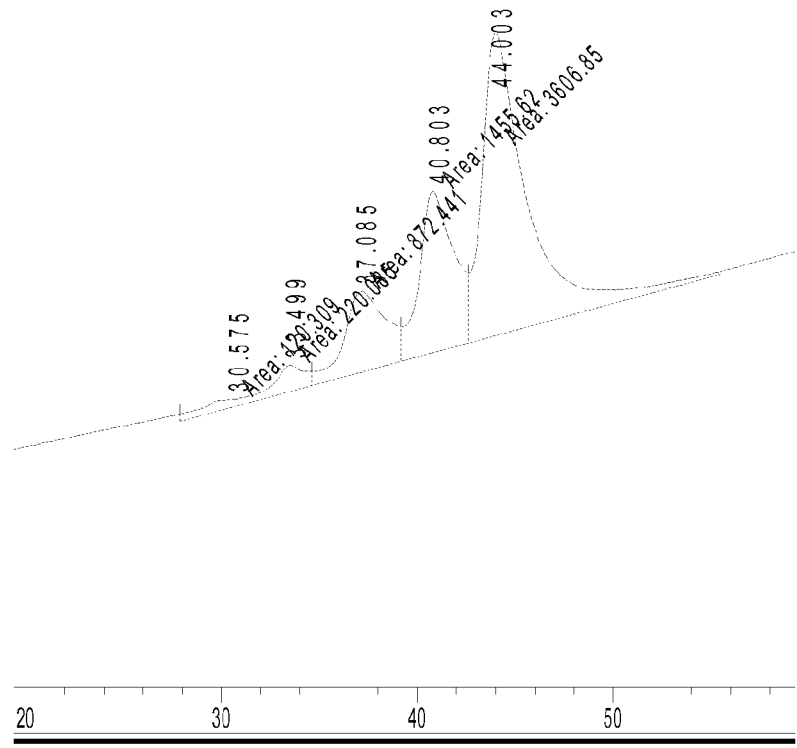

The Gla profile obtained at a column overload of 122% (IEX-HPLC analyses) when compared with a Gla profile obtained at load below capacity (IEX-HPLC analyses) can be seen in FIGS. 3A and 3B, respectively. A comparison of the distribution of Gla with overload and below load capacity can be seen in the table below:

| #Gla | % Area obtained at 122% column overload | % Area obtained at load below capacity |
|---|---|---|
| #1-8 | 0.0 | 1.8 |
| #1-9 | ~1.0 | 4.0 |
| #1-10 | 8.5 | 15.1 |
| #1-11 | 26.5 | 24.3 |
| #1-12 | 64.1 | 54.8 |

Thus, purification using 122% column overload as described above led to the removal of all detectable #1-8-Gla from the original FIX sample. There was also a decrease in the presence of #1-9- and #1-10-Gla and a consequent increase in the proportion of #1-11- and #1-12-Gla (i.e. 90.6% of active forms #1-11 and #1-12 were obtained at column overload when compared with 79.1% at below column load).

Figure 3C:
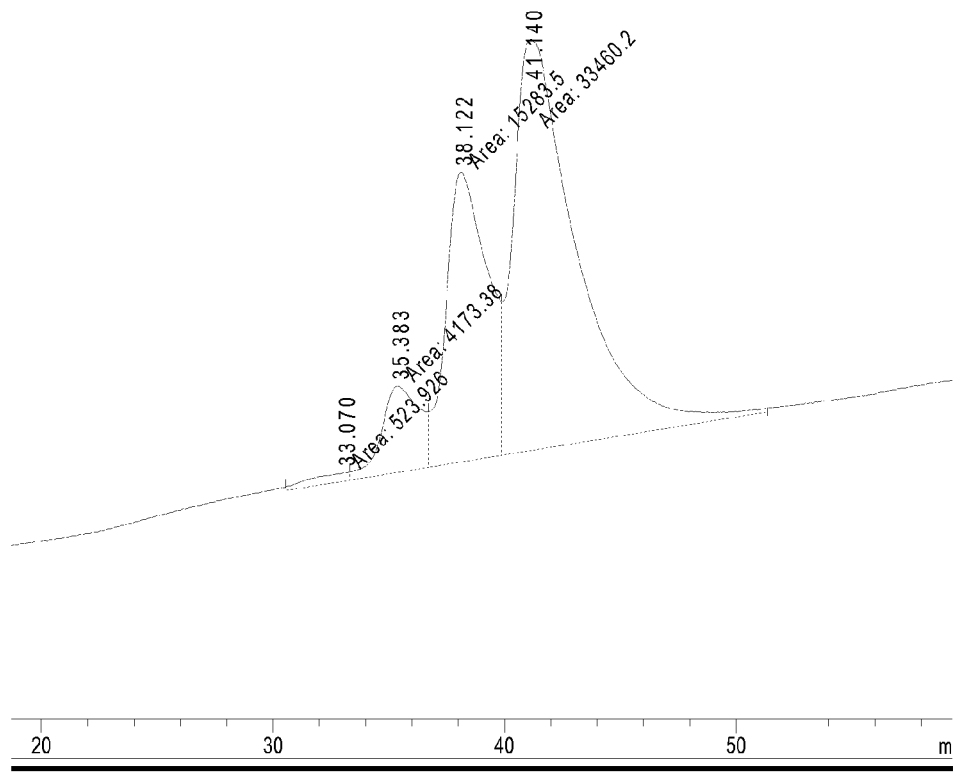
Figure 3D:
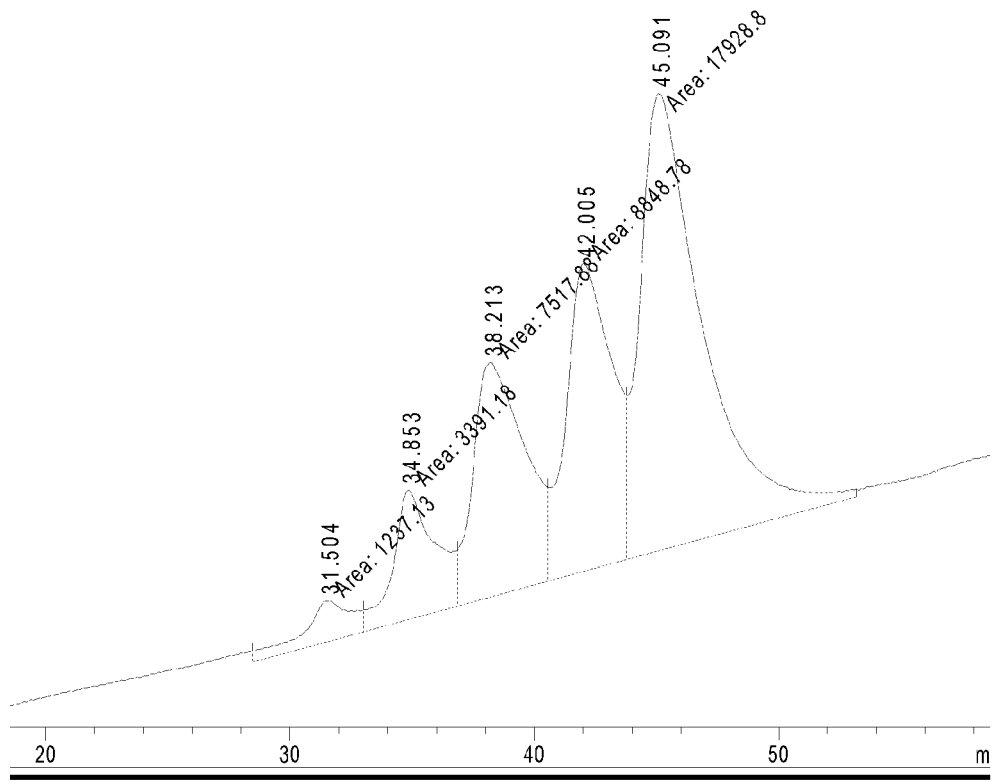

The Gla profile obtained at a column overload of 170% (IEX-HPLC analyses) when compared with a Gla profile obtained at load below capacity (IEX-HPLC analyses) can be seen in FIGS. 3C and 3D, respectively. A comparison of the distribution of Gla with overload and below load capacity can be seen in the table below:

| #Gla | % Area obtained at 170% column overload | % Area obtained at load below capacity |
|---|---|---|
| #1-8 | 0.0 | 3.2 |
| #1-9 | 1.0 | 8.7 |
| #1-10 | 7.8 | 19.3 |
| #1-11 | 28.6 | 22.7 |
| #1-12 | 62.6 | 46.1 |

Thus, purification using 170% column overload as described above led to the removal of all detectable #1-8-Gla from the original FIX sample. There was also a decrease in the presence of #1-9- and #1-10-Gla and a consequent increase in the proportion of #1-11- and #1-12-Gla (i.e. 91.2% of active forms #1-11 and #1-12 were obtained at column overload when compared with 68.8% at below column load).

Figure 3E:
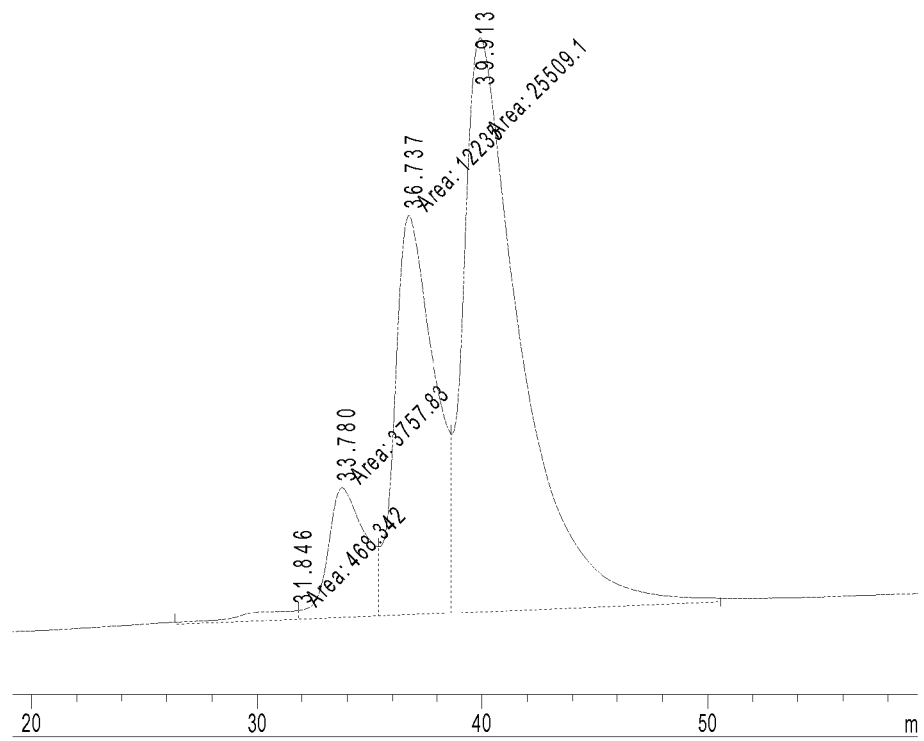
Figure 3F:
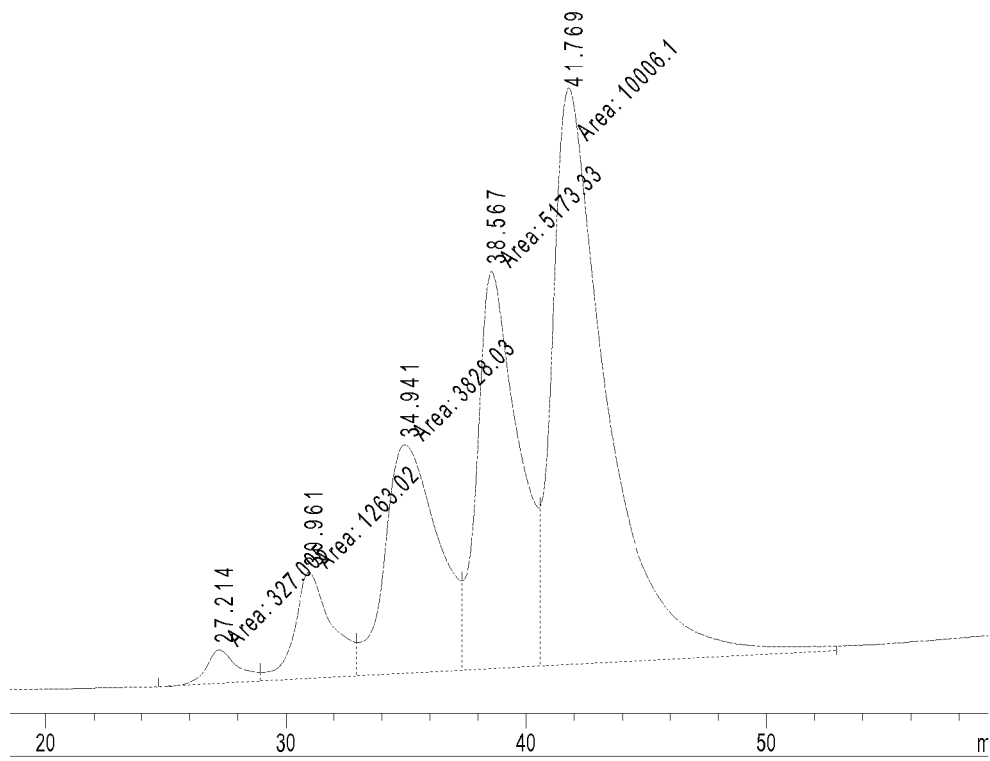

The Gla profile obtained at a column overload of 334% (IEX-HPLC analyses) when compared with a Gla profile obtained at load below capacity (IEX-HPLC analyses) can be seen in FIGS. 3E and 3F, respectively. A comparison of the distribution of Gla with overload and below load capacity can be seen in the table below:

| #Gla | % Area obtained at 334% column overload | % Area obtained at load below capacity |
|---|---|---|
| #1-8 | 0.0 | 1.6 |
| #1-9 | 1.1 | 6.1 |
| #1-10 | 9.0 | 18.6 |
| #1-11 | 29.2 | 25.1 |
| #1-12 | 60.8 | 48.6 |

Thus, purification using 334% column overload as described above led to the removal of all detectable #1-8-Gla from the original FIX sample. There was also a decrease in the presence of #1-9- and #1-10-Gla and a consequent increase in the proportion of #1-11- and #1-12-Gla (i.e. 90.0% of active forms #1-11 and #1-12 were obtained at column overload when compared with 73.7% at below column load).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The invention claimed is:

1. A method for purifying a sample of human Factor IX, comprising:
   (a) loading a sample comprising different species of human Factor IX onto an immunoaffinity chromatography material comprising a gamma-carboxyglutamic-directed antibody (Gla-directed antibody);
   wherein the amino acid sequence of the Gla-directed antibody comprises SEQ ID NO: 1 and SEQ ID NO: 2;
   wherein the different species of human Factor IX comprise different numbers of Gla residues;
   (b) eluting the sample of human Factor IX; and
   (c) selecting a fraction obtained from the elution comprising an increase in the proportion of one or both of #1-11-Gla and #1-12-Gla species of human Factor IX compared with the proportion of one or both of #1-11-Gla and #1-12-Gla species of human Factor IX in the sample being purified;
   wherein the total concentration of human Factor IX within the sample exceeds the binding ability of the immunoaffinity chromatography material.

2. The method according to claim 1, wherein the binding ability of the immunoaffinity chromatography material is exceeded by a percentage selected from the group consisting of 100, 105, 110, 115, 120, 125, 130, 140, 150, 200, 250, 500, 750, and 1000%.

3. The method according to claim 1, wherein the binding ability of the immunoaffinity chromatography material is exceeded by between 100-400%.

4. The method according to claim 1, wherein the fraction comprises a decrease in the proportion of #1-10-Gla species of human Factor IX compared with the proportion of #1-10-Gla species of Factor IX in the sample being purified.

5. The method according to claim 1, wherein the eluting comprises loading an elution buffer at a pH of between 5.0 and 8.5.

6. The method according to claim 1, wherein the eluting comprises an elution buffer comprising sodium chloride at a concentration of between 10 mM and 100 mM.

7. The method according to claim 1, wherein the divalent cation is calcium or magnesium.

8. The method according to claim 1, wherein the immunoaffinity material comprises a sepharose bead.

9. The method according to claim 1, further comprising loading an equilibration buffer prior to loading the sample and loading a wash buffer after loading the sample, wherein the equilibrium buffer and the wash buffer each comprises a calcium ion.

10. The method according to claim 9, wherein the calcium ion is present in a concentration greater than 0.5 mM.

11. The method according to claim 1, further comprising loading an equilibrium buffer prior to loading the sample at a pH of between 5.0 and 8.5.

12. The method according to claim 9, wherein the calcium ion is calcium chloride.

13. The method according to claim 1, further comprising selecting a fraction obtained from the eluted sample of Factor IX as a second sample and further purifying the second sample using anion chromatography.

14. A method for purifying a sample of human Factor IX, comprising:

loading a sample comprising different species of human Factor IX onto an immunoaffinity chromatography material comprising a gamma-carboxyglutamic-directed antibody (Gla-directed antibody);

wherein the amino acid sequence of the Gla-directed antibody comprises SEQ ID NO: 1 and SEQ ID NO: 2;

wherein the total concentration of human Factor IX within the sample exceeds the binding ability of the immunoaffinity chromatography material;

b) eluting the sample of human Factor IX;
c) selecting a fraction obtained from the elution as a second sample of human Factor IX;
d) loading the second sample of human Factor IX onto an anion exchange chromatography material;
e) eluting the second sample of human Factor IX; and
f) selecting a fraction obtained from the elution of the second sample comprising an increase in the proportion of one or both high Gla species #1-11-Gla and #1-12-Gla of human Factor IX compared with the proportion of one or both of #1-11-Gla and #1-12-Gla species of human Factor IX in the sample being purified.

15. The method of claim 13, wherein eluting the second sample is done using an eluent selected from the group consisting of ammonium acetate, ammonium chloride, sodium acetate, and sodium chloride.

16. The method of claim 13, wherein eluent is at a pH between about 5.0 to about 8.5.

17. The method according to claim 13, wherein the second sample of human Factor IX comprises a decrease in the proportion of #1-10-Gla species of human Factor IX compared with the proportion of #1-10-Gla species of Factor IX in the sample being purified.

18. The method according to claim 13, wherein the divalent cation is calcium or magnesium.

19. The method according to claim 13, wherein the immunoaffinity material comprises a sepharose bead.

* * * * *